United States Patent [19]

Case et al.

[11] 4,247,633

[45] Jan. 27, 1981

[54] REAGENT FOR COLORIMETRIC DETERMINATION OF CREATIVE PHOSPHOKINASE

[75] Inventors: Richard V. Case, Milwaukee; Louis M. Mezei, Grafton; Jack M. Siegel, Milwaukee, all of Wis.

[73] Assignee: Pabst Brewing Company, Milwaukee, Wis.

[21] Appl. No.: 27,254

[22] Filed: Apr. 5, 1979

Related U.S. Application Data

[63] Continuation of Ser. No. 731,577, Oct. 12, 1976, abandoned, which is a continuation-in-part of Ser. No. 666,462, Mar. 13, 1976, abandoned.

[51] Int. Cl.$^3$ .............................. C12Q 1/50; C12N 9/96
[52] U.S. Cl. .......................................... 435/17; 435/14; 435/15; 435/26; 435/188; 435/189; 435/194
[58] Field of Search ...................... 435/4, 17, 26, 188, 435/194, 15, 14

[56] References Cited

U.S. PATENT DOCUMENTS

| | | | |
|---|---|---|---|
| 3,540,984 | 11/1970 | Deutsch | 435/15 |
| 3,764,478 | 10/1973 | Bergmeyer et al. | 435/4 |
| 3,791,931 | 2/1974 | Thum et al. | 435/26 X |
| 3,929,580 | 12/1975 | Forgione et al. | 435/188 X |
| 4,012,286 | 3/1977 | Sanderson et al. | 435/14 |

OTHER PUBLICATIONS

Arigad et al., Reduced Nicotinamide Dinucleotide Phosphate Diaphorase from *Bacillus subtilis,* European J. Biochem., vol. 1, 1967 (pp. 102–109).
Warren, W. A., Activation of Serum Creatine Kinase by Dithiothreitol, Clinical Chemistry, vol. 18, No. 5, 1972 (pp. 473–475).

*Primary Examiner*—David M. Naff
*Attorney, Agent, or Firm*—Richard L. Johnston

[57] ABSTRACT

An all-in-one reagent is provided for the quantitative colorimetric determination of creatine phosphokinase in blood serum or plasma wherein the tetrazolium dye, 2-(p-iodophenyl)-3-(p-nitrophenyl)-5-phenyl tetrazolium chloride (INT), preferably together with an electron transport such as diaphorase, and compatible substances which are enzymatically converted by creatine phosphokinase to an end product that will reduce said dye from its normally colorless state to a colored reduced state are combined into a homogeneous composition which can be dried to a stable reagent.

14 Claims, 2 Drawing Figures

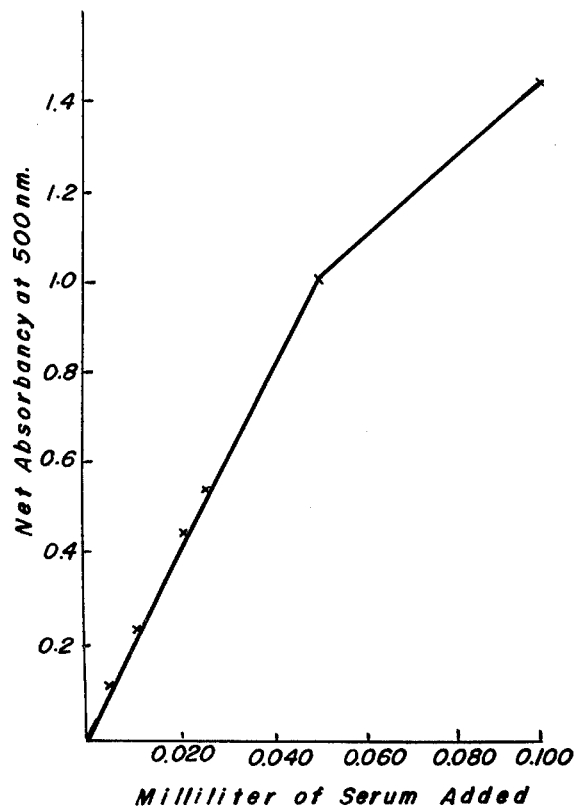
FIG.1  Proportionality of Absorbancy Measurements to Amount of CPK in Test Sample
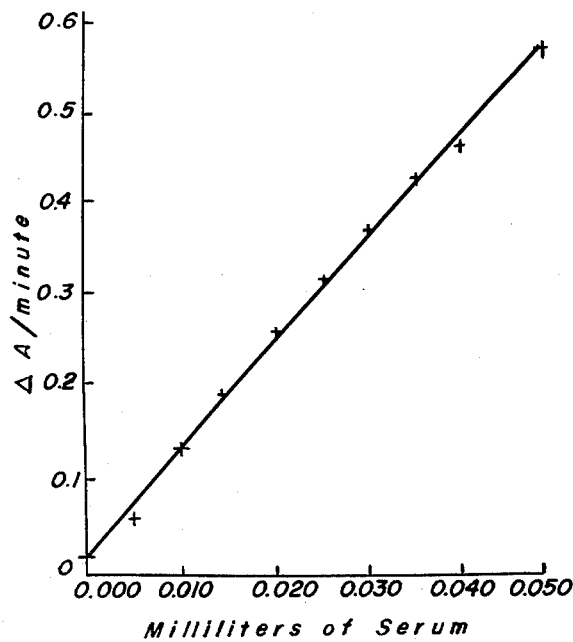
FIG.2  Proportionality of Rate of Increase of Absorbancy to Amount of CPK in Test Sample

REAGENT FOR COLORIMETRIC DETERMINATION OF CREATIVE PHOSPHOKINASE

This application is a continuation of application Ser. No. 731,577 filed Oct. 12, 1976, abandoned, which is a continuation-in-part of application Ser. No. 666,462 filed Mar. 13, 1976, abandoned.

BACKGROUND

Creatine kinase (also known as creatine phosphokinase, abbreviated CPK) is an enzyme that is present in the cells of heart muscle and other tissues of the human body, and it catalyzes the following reaction:

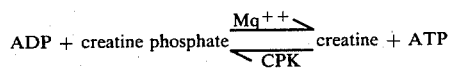   I.

where:
ADP=adenosine 5'-diphosphate
ATP=adenosine 5'-triphosphate

Measurement of the concentration of CPK in the circulating blood of patients suspected of having suffered a "heart attack" has proven to be of great value in the diagnosis of myocaridal infarction. A few hours after the occurrence of a myocardial infarction, CPK is released from the heart tissue into the circulating blood. Thereafter, the high circulating concentration of CPK decreases spontaneously over a period of several days returning to the low normal values. There are very few circumstances other than a myocardial infarction that result in elevated levels of CPK in the circulating blood. The detection of high levels of CPK therefore is indicative of the recent occurrence of a myocardial infarction.

The measurement of CPK is performed on a sample of the patient's blood that has been treated to obtain the blood serum or plasma. Because the quantity of enzyme in the serum or plasma is very minute even at elevated levels, the amount of enzyme is measured by its catalytic activity, i.e., its effect on the rate of reaction in vitro. Under certain conditions, the rate of reaction is directly proportional to the amount of CPK in the sample, and it can be measured by determining the rate of disappearance or appearance of one of the reactants or products.

The following is an example of a method currently in use for the determination of CPK that is based on the rate of formation of ATP, a product of the reaction. ATP can be measured by means of the following reactions [Kornberg, A., J. Biol. Chem. 182, 779 (1950)]

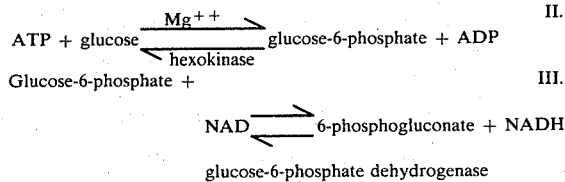

where:
NAD=nicotinamide-adenine dinucleotide
NADH=nicotinamide-adenine dinucleotide reduced.

In the presence of appropriate concentrations of glucose, hexokinase, NAD, glucose-6-phosphate dehydrogenase and Mg++ in an aqueous solution, the rate of NADH formation is directly proportional to the rate of ATP formation, and thus to the quantity of CPK as described above. NADH absorbs light with an absorption maximum at 340 nanometers (nm) and this property can be used to measure the rate of formation of NADH. A procedure has been described, which measures CPK by determining the rate of increase of absorbance at 340 nm in an aqueous solution [Oliver, I. T. Biochem. J. 61, 116 (1955)]. This procedure is known as the "UV kinetic" method of analysis where UV stands for ultraviolet absorption associated with NADH.

The UV kinetic method offers the advantage that all ingredients necessary for the measurement of CPK are present in the reaction mixture but, at the same time, it suffers from several disadvantages. The application of this procedure to the rapid assay of large numbers of samples requires expensive, specialized equipment to measure the rate of change of absorbance. The sensitivity of the technique is limited by the relatively low molar absorbancy of NADH (Specifications and Criteria for Biochemical Compounds, Publication 1344, National Academy of Science, Washington, D.C. 1967). Because of the minute amounts of CPK present, the changes in absorbance are frequently so small as to tax the accuracy of the instrument used in making the measurement, thereby creating uncertainty in the values obtained for CPK.

Alternatively, one can carry out the enzyme catalyzed reaction for a definite period of time, stop the reaction and add a chromogenic reagent which reacts with one of the products to form a colored substance. This approach, known as the colorimetric method, has the following advantages: (1) total absorbance rather than rate of change of absorbance is measured, so that simpler measuring equipment can be used, (2) the enzymic reaction can be carried out for a longer period of time to enhance the amount of product formed, and (3) the chromogenic reagent can be selected to give a greater absorbancy than does NADH. The second and third conditions both offer the possibility of increasing the sensitivity of the test. Another advantage is that the measurement of the end product and the enzymic reaction need not be carried out concurrently, which makes it convenient to perform tests on a large number of samples.

The colorimetric method has been applied to the determination of CPK by other workers, but each of the methods described suffer from certain defects. Thus, in one of the methods currently in use, ADP produced in reaction I (run from right to left) is measured by means of the following reaction:

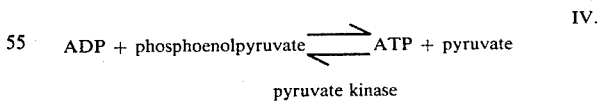   IV.

pyruvate kinase

V. Pyruvate+2,4-dinitrophenylhydrazine→hydrazone [Nuttall, F. Q. and Wedin, D. S., J. Lab. Clin. Med. 68, 324 (1966)] This procedure suffers from the disadvantage that 2,4-dinitrophenylhydrazine does not react exclusively with pyruvate, and other compounds present in the sample or formed during the enzymic reaction can interfere.

Kuby, Noda, and Lardy, [J. Biol. Chem. 209, 191 (1954)], have described a procedure in which the creatine phosphate formed in reaction I (run from right to left) is measured after decomposing it to creatine and phosphate. The phosphate can be quantitated by conversion to a phosphomolybdic acid complex followed by reduction [Fiske, C. H. and Subbaow, Y., J. Biol. Chem. 66, 375 (1925)]. This procedure suffers from interference due to phosphate that is normally present in serum. Decomposition of ATP and ADP can also produce interfering phosphate.

The determination of either ATP or creatine in reaction I (run from left to right) has the advantage that the reaction from left to right reportedly occurs 2 to 5 times faster than the reverse reaction [Ennor, A. H. and Rosenberg, H., Biochemical J. 57, 203 (1954); J. A. Demetriou, P. A. Drewes, and J. B. Gin, *Clinical Chemistry Principles and Technics* (Second Edition), R. J. Henry, D. C. Cannon and J. W. Winkelman, Eds., Harper and Row, New York, N.Y., 1974, p. 898, so that these methods are inherently more sensitive by that factor. Creatine may be measured by its reaction with diacetyl in alkaline solution in the presence of a phenol to enhance the color. Ennor and Rosenberg have described such a procedure in which the phenol was alpha naphthol. This method is subject to potential interference by substances that may be present in blood and the requirement for strong alkali is hazardous to the analyst.

In U.S. Pat. No. 3,929,580 a diagnostic reagent for the detection of CPK is prepared consisting of three individual compositions arranged in layers on a carrier and separated by physical barriers in order to impart stability to the reagent. Each of the layers must be adjusted to a limited range of pH values and pH range for one layer is not compatible with that in the other two layers.

OBJECTS

One of the objects of the present invention is to provide an all-in-one homogeneous composition which can be dried to a stable reagent for the quantitative analysis of CPK.

Another object of the present invention is to provide a new and improved process and composition for the quantitative determination of CPK which is especially applicable to the quantitative analysis of CPK in blood serum or plasma.

Other objects and advantages of the invention will be apparent from the following description in conjunction with the accompanying drawings.

THE DRAWINGS

In the drawings:

FIG. 1 is a graphical representation showing the proportionality of absorbancy measurements to the amount of CPK in test samples of blood serum, and FIG. 2 is a graphical representation showing the proportionality of the rate of increase of absorbancy to amount of CPK in test samples of blood serum.

BRIEF SUMMARY OF THE INVENTION

In accordance with the present invention, an all-in-one reagent and a process are provided for the quantitative colorimetric determination of creatine phosphokinase in blood serum or plasma wherein the tetrazolium dye, 2-(p-iodophenyl)-3-(p-nitrophenyl)-5-phenyl tetrazolium chloride (INT), preferably together with an electron transport such as diaphorase, and compatible substances which are enzymatically converted by creatine phosphokinase to an end product that will reduce said dye from its normally colorless state to a colored reduced state are combined into a homogeneous composition which can be dried to a stable reagent.

DETAILED DESCRIPTION OF THE INVENTION

The invention is based upon the concept of adding to a sample of blood serum or plasma or other liquid containing a quantity of CPK to be determined an all-in-one reagent including the normally colorless dye INT and substances compatible at a predetermined pH which will be enzymatically converted by CPK to an end product that will reduce INT to a reduced colored form so as to impart color to the liquid, whereby the absorbancy of the colored liquid is proportional to the quantity of CPK.

This can be accomplished, for example, by combining the following compatible substances to form a stable reagent which is added to the liquid to be analyzed:

(a) ADP, creatine phosphate and a compatible ionizable magnesium compound in sufficient amount to convert creatine phosphate and ADP to creatine and ATP in the presence of CPK, (b) glucose and hexokinase in sufficient amount to convert ATP to glucose-6-phosphate and ADP, (c) NAD or NADP and glucose-6-phosphate dehydrogenase in sufficient amount to convert said glucose-6-phosphate and said NAD or NADP to 6-phosphogluconate and NADH or NADPH, (d) INT and diaphorase in sufficient amount to produce NAD or NADP and reduced INT, and measuring the absorbancy of the resultant sample as compared with a reagent blank representing zero absorbance, the absorbancy found in a predetermined time period being directly proportional to the amount of CPK in the sample.

In the foregoing procedure, (a) is illustrated by equation I, (b) is illustrated by equation II, (c) is illustrated by equation III or the following equation:

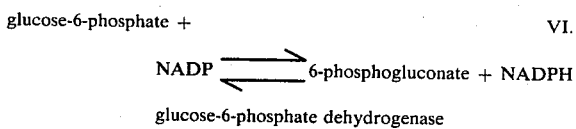

where:

NADP = nicotinamide-adenine dinucleotide phosphate

NADPH = nicotinamide-adenine dinucleotide phosphate reduced;

and (d) is illustrated by the following equations:

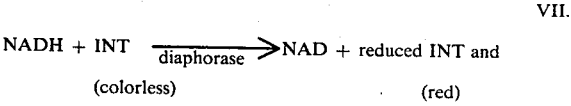

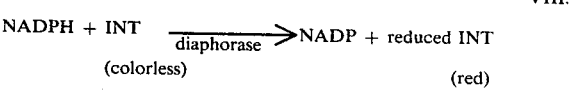

Certain other additions are preferably made for specific purposes. For example, it is desirable to add reduced glutathione or other compatible sulfhydryl reducing agent effective to maintain enzyme activity. It is also desirable to add piperazine-N,N'-bis-(2-ethane sulfonate) or other compatible buffering agent effective to maintain pH preferably pH 5.5 to 6.5. adenosine 5'-phosphate (AMP) or another compatible inhibitor can be added which is effective to inhibit side reactions.

After a predetermined time period, preferably about ten minutes from the time the reagents are added to the sample, the enzymatic reactions are stopped by reducing the pH enough to stop the reactions without adversely affecting the color development. For this purpose, acetic acid is preferred although other acids, e.g., hydrochloric and sulfuric can be used.

Reaction VI is preferred over reaction III because of greater specificity of NADP in promoting the desired reaction.

In reactions VII and VIII, the enzyme diaphorase acts as a catalyst. Both reactions are effective in promoting the reduction of INT.

This method of analysis can be carried out in the kinetic mode in which the greater molar absorbancy (Am) of the reduced INT (Am=18,000) relative to the Am for NADH (Am=6,200) eliminates some of the deficiencies of the "UV kinetic" procedure. This method also can be carried out in the stopped reaction mode. In the latter mode there is greater accumulation of the reduced INT and greater flexibility due to separation of the enzymic reaction from the absorbancy measurements. The ingredients required for the complete reaction may be added individually to the reaction vessel or they may be combined for greater convenience.

In the preferred embodiment of this invention, all assay reactants are combined in a single reagent which can be freeze-dried for long term storage. To perform a test for CPK, the regent may be used directly, or if it is freeze dried, it is reconstituted by dissolving a specified amount in a measured volume of distilled water. The resulting solution contains all of the ingredients needed for the quantitative determination of CPK.

The invention will be further illustrated but is not limited by the following examples in which the quantities are stated in parts by weight unless otherwise indicated.

EXAMPLE I

To 5,750 ml distilled water were added 29.73 grams D-glucose, 36.11 grams adenosine 5'-phosphate, 250.0 grams sodium piperazine-N,N'-bis-(2-ethane sulfonate), 6.245 grams sodium adenosine 5'-diphosphate, 13.54 grams sodium nicotinamide adenine dinucleotide phosphate, and 82.5 ml of 2.5 M magnesium chloride. The pH was adjusted to 6.08 with 32 ml 5 N NaOH and the following were added: 85.4 grams disodium creatine phosphate, 1,500 ml distilled water containing 3.764 grams 2-(p-iodophenyl)-3-(p-nitrophenyl)-5-phenyl tetrazolium chloride, and 25.90 grams glutathione reduced. The pH was adjusted to 6.00 with 23 ml 5 N NaOH and the following were added: 4,950 units of glucose-6-phosphate dehydrogenase, 14,700 units of hexokinase and 42,600 units of diaphorase. The solution was stirred slowly at room temperature for 15 minutes, and adjusted to a final volume of 8,250 ml with distilled water. Following this adjustment, the solution was filtered through a series of 142 mm diameter Millipore filters consisting of an AP 25 glass fiber pre-filter, followed by 8, 3 and 0.45 micron mixed cellulose ester filters. Aliquots of 5.50 ml. of the filtered solution were dispensed into each of 1,456 amber glass 13 ml capacity serum vials, the vials were placed in a Virtis Model 41 sublimator equipped for internal stoppering and freeze-dried for a sufficient period of time to obtain the desired degree of dryness. The sublimator chamber was brought to atmospheric pressure with dry nitrogen, and the vials were stoppered prior to opening the chamber. The moisture content determined by Karl Fisher titration was found to be 3.8%.

When the reagent is prepared in accordance with Example I, and reconstituted by dissolving the contents of 1 vial in 5.50 ml of distilled water, each milliliter will contain no less than the following quantities of each ingredient:

| | |
|---|---|
| Adenosine 5'-diphosphate (ADP) | 1.5 micromoles |
| Adenosine 5'-phosphate (AMP) | 12 micromoles |
| Creatine phospate | 20 micromoles |
| D-Glucose | 20 micromoles |
| Glutathione, reduced | 10 micromoles |
| Magnesium chloride | 25 micromoles |
| Nicotinamide-adenine dinucleotide phosphate (NADP) | 1.5 micromoles |
| 2-(p-iodophenyl)-3-(p-nitrophenyl)-5-phenyl tetrazolium chloride (INT) | 0.9 micromole |
| piperazine-N,N'-bis-(2-ethane sulfonate) | 84 micromoles |
| Hexokinase (yeast) | 1.17 units* |
| Glucose-6-phosphate dehydrogenase (yeast) | 0.24 units** |
| Diaphorase (bacterial) | 4 units*** |

*One unit of activity is equivalent to one micromole phosphorus transferred from ATP to glucose per minute at 30° C. and pH 7.60 in 3.0 milliliters of aqueous reaction mixture containing 0.67 millimole D-glucose, 1.65 micromoles of adenosine 5'-triphosphate, 2.5 micromoles NADP, 0.02 millimole of magnesium chloride, 0.125 millimole of triethanolamine and 10 units of glucose-6-phosphate dehydrogenase.

**One unit of activity is equivalent to the reduction of one micromole of NADP per minute at 30° C. and pH 8.00 in 2.9 milliliters of aqueous reaction mixture containing 3 micromoles sodium D-glucose-6-phosphate, 1.25 micromoles NADP, 0.03 millimole magnesium chloride and 0.25 millimole of glycylglycine.

***One unit of activity is equivalent to an increase in absorbance at 500 nm of stet per minute due to the reduction of INT with nicotinamide-adenine dinucleotide phosphate reduced (NADPH) as substrate at 30° C. and pH 7.50 in 1.0 milliletr of aqueous reaction mixture containing 5 micromoles of NADPH, 0.67 milligram of INT, 0.11 millimole of tris-(hydroxymethyl)-aminomethane and 0.05 microliter of Tergitol NPX.

EXAMPLE II

Reagent for the quantitative colorimetric determination of CPK prepared in freeze-dried form in vials as in Example I, was reconstituted by adding 5.50 ml of distilled water to each vial used and dissolving the contents by gentle swirling. Quantities of 1.0 ml reconstituted reagent were dispensed into a series of test tubes using one tube for each sample of serum to be analyzed plus one tube for a reagent blank. The tubes were placed in a 37° C. water bath for 5 minutes and at timed intervals (e.g., 30 seconds) 0.005–0.100 ml quantities of a commercial control serum known to contain a very high level of CPK were added to the series of tubes containing the reagent, the contents mixed and the tubes returned to the water bath. Exactly 10 minutes later, and in the same time sequence used above, 5.0 ml of 0.1 N acetic acid were added to each tube and mixed thoroughly. The absorbance at 500 nm of each test solution was measured in a Gilford Model 2400S spectrophotometer adjusted to zero absorbance using the reagent blank. The absorbance was found to be directly proportional to the amount of CPK in the serum sample, i.e., directly proportional to the sample volume up to a volume of 0.050 ml of serum.

By means of an independent method of calibration, which is not a part of the present invention, it was established that an absorbancy of $5.40 \times 10^{-4}$ is equivalent to 1 international unit of CPK per liter of serum. Applying this factor to the absorbancy values observed above, it was found that the observed assay values were directly proportional to the amount of CPK over the range of zero to 1,859 units of activity. The data are summarized in Table 1 and FIG. 1.

TABLE I

Proportionality of absorbancy measurement to amount of CPK in test sample

| Sample Volume (Millileters) | Net Absorbance | Creatine Kinase Activity |
|---|---|---|
| Reagent blank | (0.000) | 0 |
| 0.005 | 0.099 | 183 |
| 0.010 | 0.215 | 398 |
| 0.020 | 0.431 | 798 |
| 0.025 | 0.526 | 974 |
| 0.050 | 1.004 | 1,859 |
| 0.100 | 1.445 | 2,676 |

EXAMPLE III

Reagent prepared as in Example I in freeze-dried form in vials was reconstituted by adding 5.50 ml of distilled water to each vial used, and dissolving the contents by gentle swirling. Quantities of 3.0 ml reconstituted reagent were dispensed into a series of rectangular glass cuvettes with a 1.0 centimeter path length. The cuvettes were brought to temperature in a 37° C. water bath over a period of 2 to 3 minutes and transferred to the temperature controlled cuvette chamber of a Gilford 2400S recording spectrophotometer with the temperature set at 37° C. Portions of a human pooled serum known to contain a high level of CPK were added to the cuvettes, the contents quickly mixed and the increase in absorbance at 500 nm was recorded as a function of time. The rates of change of absorbance, $\Delta A$/minute, were calculated by drawing a tangent to the linear portion of the curve for each sample. The results are given in Table 2 and FIG. 2, and show a direct proportionality between the rate of change of absorbance and the amount of CPK in the sample, i.e. directly proportional to the aliquant volume up to a volume of 0.050 ml of serum.

TABLE 2

Proportionality of rate of increase of absorbance at 500 nm to amount of creatine kinase in test sample

| Sample Volume (millileter) | Reaction Rate ($\Delta A$ per minute) |
|---|---|
| 0.005 | 0.065 |
| 0.010 | 0.130 |
| 0.015 | 0.193 |
| 0.020 | 0.254 |
| 0.025 | 0.306 |
| 0.030 | 0.362 |
| 0.035 | 0.416 |
| 0.040 | 0.462 |
| 0.050 | 0.580 |

The commercial application of an in vitro diagnostic reagent for the determination of CPK requires that the reagent is useful over an extended period of time when kept under proper storage conditions, e.g. 6–12 months, that it is convenient to use, that it gives a linear response over a wide range of CPK levels in the specimens analyzed, that it has a low reagent blank value, and that it gives reproducible results. The reagent as prepared in Example I embodies many innovations in its composition and manner of its formulation which impart to it the qualities described above. Several of the innovations are as follows:

1. Magnesium is preferably added in the form of the chloride salt instead of the acetate salt which has been used traditionally to catalyze reactions I and II. This innovation greatly facilitated the freeze-drying of the reagent to obtain a uniformly fine-structured dry mass suitable for reconstitution.

2. The quantity of hexokinase in the reagent is preferably adjusted to give a final concentration in the reaction mixture of 1.17 to 4.50 units per ml.

3. The quantity of glucose-6-phosphate dehydrogenase in the reagent is preferably adjusted to give a final concentration in the reaction mixture of 0.24 to 1.25 units per ml.

4. The quantity of diaphorase in the reagent is preferably adjusted to give a final concentration in the reaction mixture of 4 to 47 units per ml. The innovations described in 2, 3 and 4 all contribute to extend the range of linear response to CPK, and to extend the shelf life of the reagent.

5. The pH of the reagent is preferably adjusted to a value of 5.5 to 6.5, thereby promoting the stability of the final reagent.

6. After all ingredients have been added the reagent solution is preferably allowed to stand at room temperature for at least 15 minutes and then filtered to remove any reduced INT that may be present, thereby insuring a low blank value in the final reagent.

7. The freeze drying of the reagent is preferably continued until the water content is reduced to a maximum of 7%. This degree of dryness is required to promote the required stability of the final product.

8. The vials containing the freeze-dried reagent are sealed under an atmosphere of dry nitrogen gas to enhance the stability of the final product.

While each of the above-mentioned innovations plays a role in the production of an in vitro diagnostic reagent exhibiting all of the highly desired properties described above for a successful commercial product, it is possible to obtain a somewhat less satisfactory but useful product by applying only one or more of the foregoing innovations.

The invention is hereby claimed as follows:

1. An all-in-one reagent for the quantitative colorimetric determination of creatine phosphokinase (CPK) in blood serum or plasma, or other liquid consisting essentially of the following ingredients:
    (a) adenosine 5'-diphosphate (ADP), creatine phosphate and a source of magnesium ions in sufficient amount to convert creatine phosphate and ADP to creatine and adenosine 5'-triphosphate (ATP) in the presence of CPK,
    (b) glucose and hexokinase in sufficient amount to convert ATP to glucose-6-phosphate and ADP,
    (c) nicotinamide-adenine dinucleotide (NAD) or nicotinamide-adenine dinucleotide phosphate (NADP) and glucose-6-phosphate dehydrogenase in sufficient amount to convert said glucose-6-phosphate and said NAD or NADP to 6-phosphogluconate and NADH or NADPH,
    (d) 2-(p-iodophenyl)-3-(p-nitro-phenyl)-5-phenyl tetrazolium chloride (INT) and a diaphorase in sufficient amount to produce NAD or NADP and reduced INT,
    (e) a buffer which maintains the pH of said reagent between 5.5 and 6.5 when all ingredients are dissolved in water,
    (f) reduced glutathione in sufficient amount to maintain enzyme activity, and
    (g) adenosine 5'-phosphate in sufficient amount to inhibit side reactions.

2. A reagent as claimed in claim 1 in the form of an aqueous solution having a pH of 5.5 to 6.5.

3. A reagent as claimed in claim 1 in which the buffer of (e) is piperazine-N,N'-bis-(2-ethane sulfonate).

4. A reagent as claimed in claim 1, which contains magnesium chloride as a source of magnesium ions.

5. A reagent as claimed in claim 1 in which the hexokinase concentration is 1.17 to 4.5 units per ml.

6. A reagent as claimed in claim 1 in which the glucose-6-phosphate dehydrogenase concentration is 0.24 to 1.25 units per ml.

7. A reagent as claimed in claim 1 in which the diaphorase concentration is 4 to 47 units per ml.

8. A reagent as claimed in claim 1 formed by preparing an aqueous solution containing all of the ingredients, allowing the solution to stand at room temperature for at least 15 minutes and then filtering the solution to remove reduced INT.

9. A reagent as claimed in claim 1 in the form of an aqueous solution containing concentrations of ingredients as follows:
   (a) hexokinase 1.17 to 4.5 units per ml.,
   (b) glucose-6-phosphate dehydrogenase 0.24 to 1.25 units per ml.,
   (c) diaphorase, 4 to 47 units per ml., and in forming the reagent, the solution of ingredients having a pH of 5.5 to 6.5 is allowed to stand at room temperature for at least 15 minutes and filtered to remove reduced INT.

10. A reagent as claimed in claim 1 formed by freeze-drying an aqueous solution of the ingredients to reduce the moisture content to a maximum of 7% by weight, as measured by Karl Fisher titration.

11. An all-in-one reagent for the quantitative colorimetric determination of creatine phosphokinase in blood serum or plasma, or other liquid consisting essentially of the following ingredients dissolved in water: adenosine 5'-diphosphate (ADP), adenosine 5'-phosphate (AP), creatine phosphate (CP), diaphorase, D-glucose, glucose-6-phosphate dehydrogenase, glutathione reduced, hexokinase, 2-(p-iodophenyl)-3-(p-nitrophenyl)-5-phenyl tetrazolium chloride (INT), magnesium chloride, nicotinamide-adenine dinucleotide phosphate (NADP), and piperazine-N,N'-bis(2-ethane sulfonate), the quantity of ADP and magnesium chloride being sufficient to convert the creatine phosphate to creatine and adenosine 5'-triphosphate (ATP) in the presence of creatine phosphokinase, the quantity of D-glucose and hexokinase being sufficient to convert the ATP to glucose-6- phosphate and ADP, the quantity of NADP and glucose-6-phosphate dehydrogenase being sufficient to convert the glucose-6-phosphate and the NADP to 6-phosphogluconate and reduced NADP, the quantity of INT and diaphorase being sufficient to produce NADP and reduced INT, the quantity of piperazine-N,N'-bis(2-ethane sulfonate) being sufficient to maintain a pH between 5.5 and 6.5, the quantity of reduced glutathione being sufficient to maintain enzyme activity and the quantity of AP being sufficient to inhibit side reactions, said reagent being formed by dissolving all the ingredients in water to produce a solution having a pH of 5.5 to 6.5, allowing the solution to stand at room temperature for at least 15 minutes and filtering the solution to remove any reduced INT.

12. A reagent as claimed in claim 11 in freeze-dried form containing a maximum of 7% by weight water, as measured by Karl Fisher titration.

13. An all-in-one reagent for the quantitative colorimetric determination of creatine phosphokinase in blood serum or plasma, or other liquid consisting essentially of the following ingredients dissolved in water: adenosine 5'-diphosphate (ADP), adenosine 5'-phosphate (AP), creatine phosphate (CP), diaphorase, D-glucose, glucose-6-phosphate dehydrogenase, glutathione reduced, hexokinase, 2-(p-iodophenyl)-3-(p-nitrophenyl)-5-phenyl tetrazolium chloride (INT), magnesium chloride, nicotinamide-adenine dinucleotide (NAD), and piperazine-N,N'-bis(2-ethane sulfonate), the quantity of ADP and magnesium chloride being sufficient to convert the creatine phosphate to creatine and ATP in the presence of creatine phosphokinase, the quantity of D-glucose and hexokinase being sufficient to convert the ATP to glucose-6-phosphate and ADP, the quantity of NAD and glucose-6-phosphate dehydrogenase being sufficient to convert the glucose-6-phosphate and the NAD to 6-phosphogluconate and reduced NAD, the quantity of INT and diaphorase being sufficient to produce nicotinamide-adenine dinucleotide and reduced INT, the quantity of piperazine-N,N'-bis(2-ethane sulfonate) being sufficient to maintain a pH between 5.5 and 6.5, the quantity of reduced glutathione being sufficient to maintain enzyme activity and the quantity of AP being sufficient to inhibit side reactions, said reagent being formed by dissolving all the ingredients in water to produce a solution having a pH of 5.5 to 6.5, allowing the solutions to stand at room temperature for at least 15 minutes and filtering the solution to remove any reduced INT.

14. A reagent as claimed in claim 13 in freeze-dried form containing a maximum of 7% by weight water, as measured by Karl Fisher titration.

* * * * *

UNITED STATES PATENT AND TRADEMARK OFFICE
CERTIFICATE OF CORRECTION

PATENT NO. : U.S. 4,247,633
DATED : January 27, 1981
INVENTOR(S) : RICHARD V. CASE, LOUIS M. MEZEI, and JACK M. SIEGEL It is certified that error appears in the above-identified patent and that said Letters Patent are hereby corrected as shown below:

On the title page

[54] "REAGENT FOR COLORIMETRIC DETERMINATION OF CREATIVE PHOSPHOKINASE" should read --REAGENT FOR COLORIMETRIC DETERMINATION OF CREATINE PHOSPHOKINASE--

Column 1, title should read --REAGENT FOR COLORIMETRIC DETERMINATION OF CREATINE PHOSPHOKINASE--.

Signed and Sealed this

Nineteenth Day of January 1982

[SEAL]

Attest:

*Attesting Officer*

GERALD J. MOSSINGHOFF
*Commissioner of Patents and Trademarks*